United States Patent
Skoletsky

(10) Patent No.: US 6,221,025 B1
(45) Date of Patent: Apr. 24, 2001

(54) SKIN BLOOD FLOW MEASUREMENT

(75) Inventor: Ilya Skoletsky, Beer Sheva (IL)

(73) Assignee: I. S. Medtech Ltd., Beer Sheva (IL)

( * ) Notice: Subject to any disclaimer, the term of this patent is extended or adjusted under 35 U.S.C. 154(b) by 0 days.

(21) Appl. No.: 09/462,775

(22) PCT Filed: Jul. 15, 1997

(86) PCT No.: PCT/IL97/00240

§ 371 Date: Apr. 6, 2000

§ 102(e) Date: Apr. 6, 2000

(87) PCT Pub. No.: WO98/06325

PCT Pub. Date: Feb. 19, 1998

(30) Foreign Application Priority Data

Aug. 14, 1996 (IL) .................................................... 119076

(51) Int. Cl.[7] .................................................. A61B 5/02
(52) U.S. Cl. ............................................ 600/504; 600/549
(58) Field of Search ...................................... 600/504, 506, 600/549, 555

(56) References Cited

U.S. PATENT DOCUMENTS

| | | | |
|---|---|---|---|
| 4,739,771 | * | 4/1988 | Manwaring .......................... 600/504 |
| 4,802,489 | * | 2/1989 | Nitzan .............................. 600/504 X |
| 4,859,078 | | 8/1989 | Bowman . |
| 5,205,293 | * | 4/1993 | Ito et al. ........................... 600/504 X |
| 5,207,227 | | 5/1993 | Powers . |
| 5,365,924 | | 11/1994 | Erdman . |

\* cited by examiner

*Primary Examiner*—Cary O'Connor
*Assistant Examiner*—Ryan Carter
(74) *Attorney, Agent, or Firm*—Nixon & Vanderhye P.C.

(57) ABSTRACT

Apparatus (10) for measuring skin blood flow includes apparatus (12) for applying a predetermined temperature gradient to a portion of skin, thereby to change the temperature thereat from a first temperature to a second temperature; a single temperature sensing element (14) for measuring a temperature at a selected location near the portion of skin; a control apparatus (20) for operating the apparatus (12) for applying a predetermined temperature gradient, and further for operating the temperature sensing element (14) in first and second operative modes; in the first mode the temperature sensing element (14) measuring a first reference temperature at the selected location, and in the second mode the temperature sensing element (14) being operable to measure a second temperature at the selected location; wherein second mode, the control apparatus (20) operates the apparatus (12) for applying a predetermined temperature gradient so as to maintain the predetermined gradient between the first and second temperatures; and processing apparatus (47) associated with the temperature sensing element (14) for evaluating a skin blood flow corresponding to the measured first and second temperatures, and the electrical steady state power required to maintain the predetermined temperature gradient.

11 Claims, 4 Drawing Sheets

SKIN BLOOD FLOW MEASUREMENT

FIELD OF THE INVENTION

The present invention relates to non-invasive techniques and apparatus for skin blood flow measurement.

BACKGROUND OF THE INVENTION

Measuring and/or monitoring skin blood flow is important in various medical applications, for example, in obtaining information about skin function, in treating burnt skin, skin ulcers, applying skin grafts, and in evaluation of peripheral hemodynamics.

It is known in the art to measure skin blood flow non-invasively by locally heating an area of skin and measuring a temperature difference along the surface of the skin. The heated area is cooled by a variety of heat transfer mechanisms, inter alia, conduction through and along the skin and convection by the skin blood flow. The known, assumed or measured variables include the input heating or cooling power, the temperature difference and a heat transfer factor which takes into account the various aforementioned heat transfer mechanisms. These known, assumed or measured variables are input into well known heat transfer equations to calculate the unknown blood flow.

It is known in the art to perform the aforementioned procedure with a sensor shaped like a disk. The disk includes two main elements: a centrally located heating and measuring element and a peripherally located reference measuring element. The temperature difference is measured and monitored between the central heating element and the peripheral reference element.

In one type of disk sensor, the heat power input is held constant and the temperature difference is measured. Such an arrangement is described, for example, by A. V. J. Challoner, "Accurate measurement of skin blood flow by a thermal conductance method", Medical and Biological Engineering, 1975, 13:196–201, and by S. Thalayasingam and D. T. Delpy, "Thermal clearance blood flow sensor—sensitivity, linearity and flow depth discrimination", Medical and Biological Engineering & Computing, 1989, 27:394–398.

In another type of disk sensor, the temperature difference is held constant and the heat power input is measured. Such an arrangement is described, for example, by A. Dittmar, "Skin Thermal Conductivity", in J. C. Leveque, ed., *Cutaneous Investigation In Health And Disease*, New York, Marcel Dekker, 1989, 323–335, and by P. M. Greenhalgh, J. R. Jones, and J. S. Yudkin, "The 57 mm thermal clearance probe: a non-invasive tool for measuring subcutaneous blood flow", Clinical Science, 1989, 77:121–127.

Other publications which discuss skin blood flow measurement are Arnost Fronek, "Noninvasive evaluation of the cutaneous circulation", Chapter 27, pp. 269–279, in *Vascular Diagnosis*, ed. by E. F. Bernstein, published by Mosby; Pierre G. Agache and Anne-Sophie Dupond, "Recent Advances in Non-invasive Assessment of Human Skin Blood Flow", Acta Derm Venereol, 1994, Suppl. 185:47–51; M. Nitzan et al., "Theoretical Analysis of the Transient Thermal Clearance Method for Regional Blood Flow Measurement", Medical and Biological Engineering & Computing, 1986, 24:597–601; M. Nitzan et al., "Faster Procedure for Deriving Regional Blood Flow by the Non-invasive Transient Thermal Clearance Method", Annals of Biomedical Eng., 1993, 21:259–262; G. Delhomme, W. H. Newman, B. Roussel, M. Jouvet, M. F. Bowman and A. Dittmar, "Thermal Diffusion Probe and Instrument System for Tissue Blood Flow Measurements: Validation in Phantoms and in Vivo Organs", IEEE Transactions on Biomedical Engineering, Vol. 41, No. 7, July 1994; and F. Arnaud, G. Delhomme, A. Dittmar, P. Girard, L. Netchiporouk, C. Martlet, R. Cespuglio and W. H. Newman, "A Microthermal Diffusion Sensor for Non-invasive Skin Characterization", Sensors and Actuators A, 41–42 (1994). In the latter reference, a transient thermal method was used.

French Patent 85-15-932 to CNRS (National Center of Scientific Research), Lyon, France describes a constant temperature difference sensor and was used in the above-mentioned work of Dittmar. This disk sensor has several drawbacks. First, the principle of maintaining a constant temperature difference and measuring heat power input is correctly applied when the reference temperature is constant, such as the temperature of the blood flowing underneath the skin where the sensor is attached. However, in the disk sensor the reference temperature is at the periphery of the disk. The peripheral temperature is not constant, but rather increases during measurement due to heat transferred from the central heater to the periphery of the disk. Second, this sensor has a plurality of thermocouples included between the central and peripheral portions of the disk which adversely affect the accuracy of the measurement by shunting heat away from the skin. Third, the sensor includes more than 20 elements from 6 different materials, greatly increasing manufacturing costs.

French Patent Document 9011773 to Dittmar et al. describes a sensor similar to that described in the above-mentioned French Patent 85-15-932. While the Dittmar sensor has been improved with advanced materials and technology, it retains basically the same drawbacks as in the previous sensor.

Japanese Patent No. 6-217952 describes a skin blood flow sensor which has an inner disk for temperature measurement and an outer ring and heating or cooling elements. This sensor, which has a structure that is generally similar to those of French Patent Documents 85-15-932 and 9011773, and thus also disadvantages similar thereto.

SUMMARY OF THE INVENTION

The present invention seeks to provide improved apparatus and methods for measuring skin blood flow. The present invention derives the blood flow based on a predetermined temperature difference between a first, reference temperature and a second temperature, and a controlled steady-state heat power input. A single temperature sensor is used to measure both the first temperature and the second temperature. This is accomplished by measuring the first temperature initially before applying to the skin a predetermined temperature gradient, which be either positive (by heating) or negative (by cooling), and then storing the first temperature in a memory. Unlike the prior art, the same temperature sensor is used to measure both the first and second elevated temperature, so as to easily facilitate further steady-state direct measurement of the power provided so as to maintain the second temperature level.

There is thus provided, in accordance with a preferred embodiment of the invention, apparatus for measuring skin blood flow including apparatus for applying a predetermined temperature gradient to a portion of skin, thereby to change the temperature thereat from a first temperature to a second temperature; a single temperature sensing element for measuring a temperature at a selected location near to the portion of skin; control apparatus for operating the apparatus for applying a predetermined temperature gradient and, further, for operating the temperature sensing element in first and second operative modes, in the first mode the temperature sensing element measuring a first, reference temperature at the selected location, and in the second mode the temperature sensing element being operable to measure a second temperature at the selected location, wherein, in the second mode, the control apparatus operates the apparatus for applying a predetermined temperature gradient so as to maintain the predetermined gradient between the first and second temperatures; and processing apparatus, associated with the temperature sensing element, for evaluating a skin blood flow corresponding to the measured first and second temperatures and the electrical steady-state power required to maintain the predetermined temperature gradient.

Additionally in accordance with a preferred embodiment of the present invention, there is also provided a memory associated with the temperature sensing element for storing the reference temperature.

Further in accordance with a preferred embodiment of the present invention, there is also provided a visual display, associated with the processing apparatus, for displaying at least the evaluated skin blood flow.

Additionally in accordance with a preferred embodiment of the present invention, there is also provided thermal insulation for insulating the apparatus for applying a predetermined temperature gradient and the temperature sensing element from the environment.

In accordance with an embodiment of the invention, the apparatus for applying a predetermined temperature gradient comprises electrical heating apparatus.

Further in accordance with a preferred embodiment of the present invention, the temperature sensing element is a silicon diode, and may also be used as electrical heating apparatus.

Additionally in accordance with a preferred embodiment of the present invention, each of the electrical heating apparatus and the temperature sensing element is a silicon diode which are arranged in a diode array.

In accordance with a further embodiment of the invention, there is also provided a method of measuring skin blood flow at a portion of skin, including the steps of operating a temperature sensor in touching contact with a portion of skin, so as to measure a first, reference temperature thereat;

storing the value of the first temperature;

applying a predetermined temperature gradient to the portion of skin thereby to change the temperature thereat from the first temperature to the second temperature, and stabilizing the skin temperature at the second temperature;

determining the electrical power required to maintain the predetermined temperature gradient; and evaluating a blood flow associated with the portion of skin in accordance with a predetermined relationship between skin blood flow, the steady-state electrical power required to maintain the predetermined temperature gradient, and the predetermined temperature gradient.

BRIEF DESCRIPTION OF THE DRAWINGS

The present invention will be understood and appreciated more fully from the following detailed description, taken in conjunction with the drawings in which.

DETAILED DESCRIPTION OF THE PREFERRED EMBODIMENTS

Figure 1:
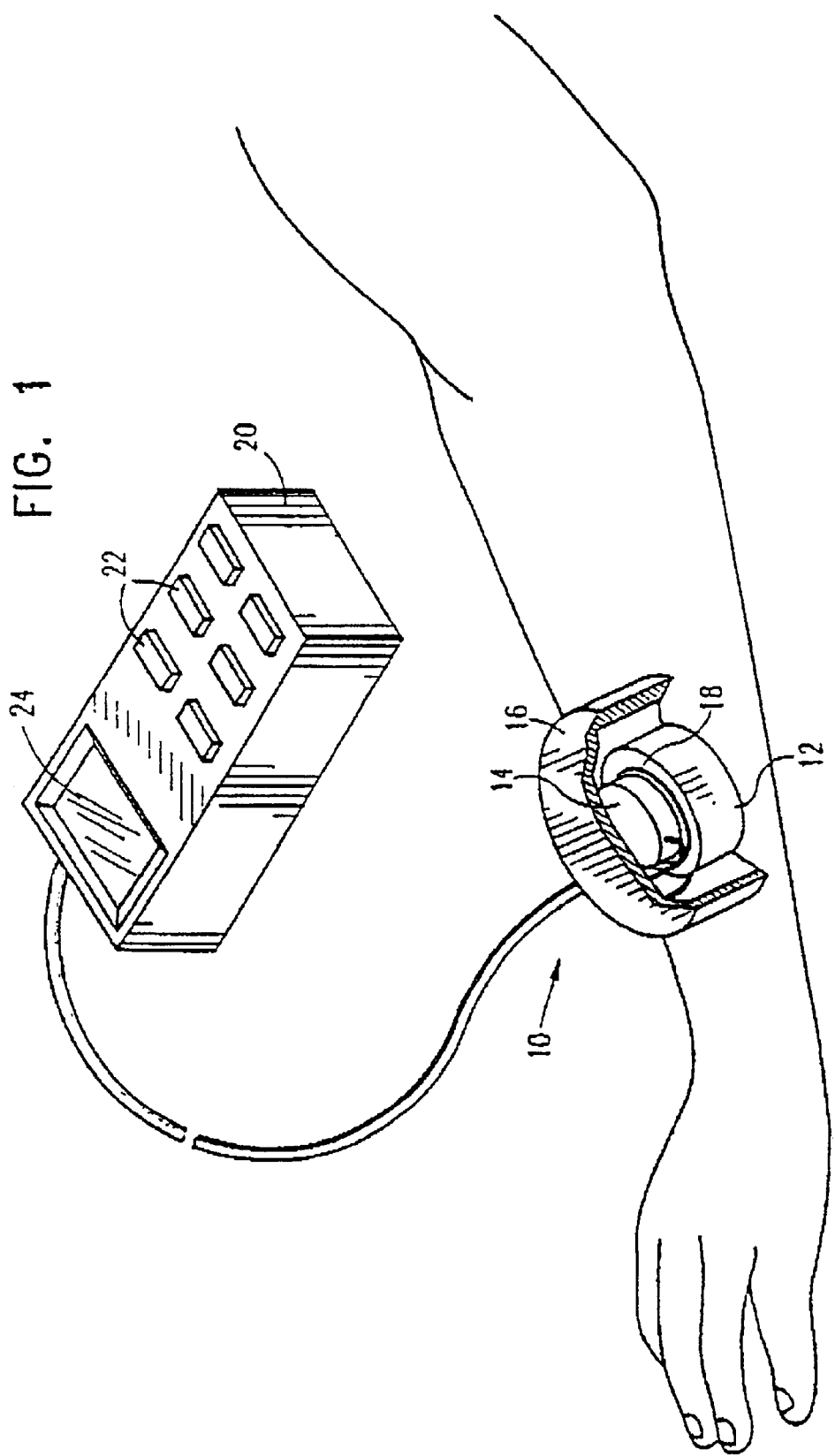
FIG. 1 is a simplified, partially cutaway, pictorial illustration of apparatus for measuring skin blood flow, constructed and operative in accordance with a preferred embodiment of the present invention.

Reference is now made to FIG. 1 which illustrates apparatus 10 for measuring skin blood flow, constructed and operative in accordance with a preferred embodiment of the present invention.

Apparatus 10 preferably includes apparatus for applying a predetermined change to the temperature of the skin, exemplified in the present embodiment by a heater 12, and a temperature sensor 14. Heater 12 may be any conventional type of heater, such as a microheater or a foil type of resistance heater, although the preferred type of heater is a silicon diode. Temperature sensor 14 may be any conventional type of temperature sensor, such as a thermocouple or thermistor, although the preferred type of sensor is a silicon diode. Heater 12 and temperature sensor 14 may be integrated together as a silicon diode array, preferably, miniaturized.

Preferably heater 12 and temperature sensor 14 are coupled inside a thermal insulator 16 which insulates them from the environment. Insulator 16 may be made of any suitable material with a poor thermal conductivity, such as plastic, and may be painted or coated with a material which diminishes radiative heat transfer loss. Temperature sensor 14 may be mounted on heater 12 by means of a thermal bond material 18, such as a thermal adhesive. Alternatively or additionally, the internal volume of insulator 16 may be filled with an insulative or encapsulating material, such as RTV.

Temperature sensor 14 and heater 12 are preferably in communication with a control and display unit 20 which processes data received from temperature sensor 14 and heater 12. Control and display unit 20 preferably includes one or more function keys 22 and a display 24 for providing a visual output indication of measured blood flow. Unit 20 may be constructed also to provide additional information, such as measured temperatures, as required.

Figure 2A:
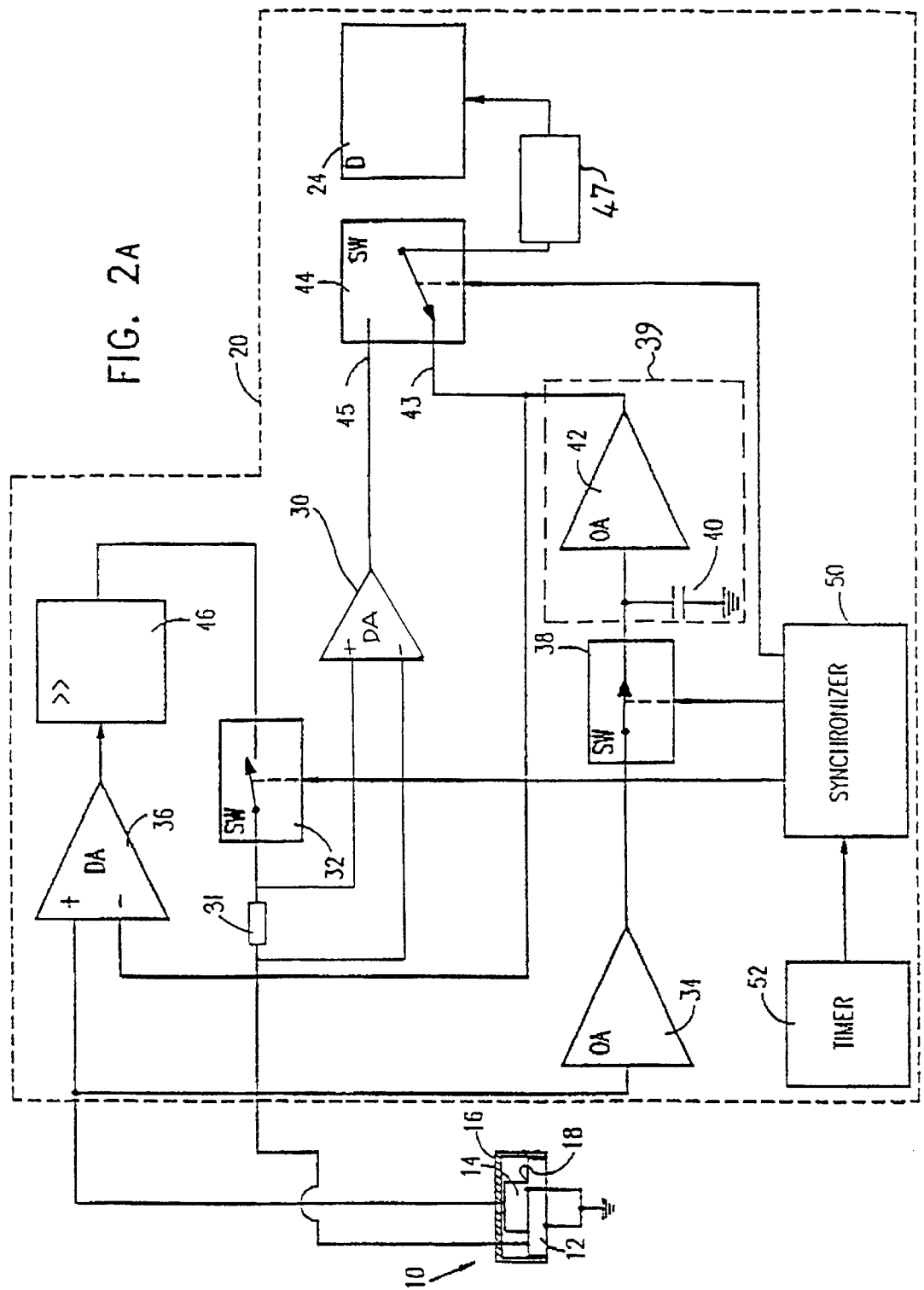
FIGS. 2A and 2B are simplified block diagrams of the apparatus seen in FIG. 1, constructed and operative in accordance with a preferred embodiment of the invention, in first and second modes of operation.
Figure 2B:
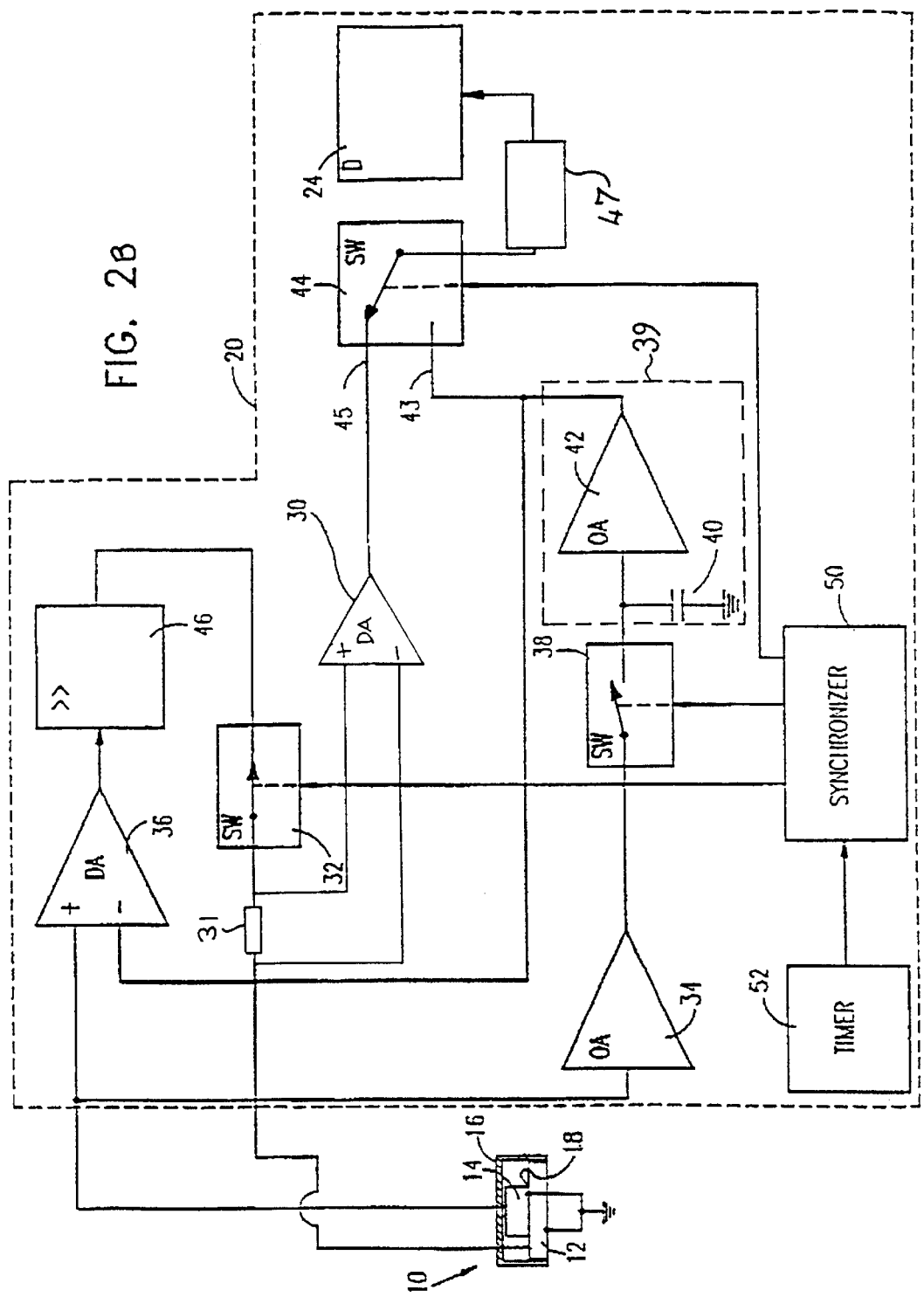

Reference is now made to FIGS. 2A and 2B which are simplified block diagrams of apparatus 10, in first and second operative modes. It will be appreciated by persons skilled in the art that the circuitry illustrated in FIG. 2 as composing control and display unit 20, is by way of example only. Accordingly, in accordance with the present invention, other circuitry and/or devices, such as suitable integrated circuit devices constructed to perform similar control and data processing functions, may be employed in place of that shown.

Both heater 12 and temperature sensor 14 are preferably grounded. In the illustrated embodiment, heater 12 is seen to be connected through a resistor 31 to an input of a differential amplifier 30 and to an output of a switch 32. Temperature sensor 14 is preferably connected to an input of an amplifier 34 and thence to a non-inverse input of a differential amplifier 36. An output of amplifier 34 is preferably connected to an input of a switch 38, whose output is connected to a memory element 39, which is seen, in the illustrated embodiment, to include a capacitor 40 and an amplifier 42. The output of switch 38 is seen to connect both to capacitor 40 and to an input of amplifier 42. An output of amplifier 42 is preferably connected to an inverse input of differential amplifier 36 and to a first input 43 of a switch 44. An output of differential amplifier 36 is preferably connected via a power amplifier 46 to an input of switch 32. An output of differential amplifier 30 is preferably connected to a second input 45 of switch 44 and thence, via suitable processing circuitry 47, to display 24. Controlling inputs of switches 32, 38 and 44 are preferably connected to corresponding inputs of a synchronizer 50 whose input is preferably connected to a timer 52. Timer 52 provides impulses to synchronizer 50 for controlling the state of switches 32, 38 and 44.

The operation of control and display unit 20, in accordance with a preferred embodiment of the invention, is now described.

Referring now to FIG. 2A, in a first mode of operation, switch 32 is open, switch 38 is closed, and switch 44 is set at input 43. Thus, initially heater 12 is not energized and temperature sensor 14 measures a first or 'reference' temperature near a portion of skin of a patient (FIG. 1). The first temperature may be measured either on top of heater 12, as illustrated, or underneath it. The first temperature is provided to display 24 via amplifier 34, switch 38, amplifier 42, switch 44, and, preferably, via processing circuitry 47. The first temperature is also stored in memory element 39, which, as described above, may be constituted by capacitor 40 and amplifier 42.

In a second mode of operation, seen in FIG. 2B, switch 32 is closed, switch 38 is opened, and switch 44 is set at input 45. A reference voltage corresponding to the first or reference temperature is provided to the input of the differential amplifier 36. An output signal from differential amplifier 36 is provided, via power amplifier 46 and switch 32, to heater 12, thereby providing a thermal feedback signal and stabilizing the temperature of heater 12 at a second temperature. In the present embodiment, in which the skin is heated, the second temperature is elevated relative to the first temperature. While neither the first nor the second temperatures are predetermined, the difference between them, or the 'temperature gradient,' is predetermined. Accordingly, as the first temperature remains generally constant, and as the temperature difference between the first and second temperatures is predetermined, the second temperature, which is regulated by the voltage/current output of power amplifier 46, is also maintained at a generally constant level.

The magnitude of the electrical steady-state power required to maintain the temperature gradient, is proportional to the heater current from power amplifier 46. Accordingly, skin blood flow may be determined by the equation:

$$V = kIU/(dT)$$

where
 V=skin blood flow
 k=coefficient which is dependent, inter alia, upon thermal conductance of skin and thermal properties of blood,
 I=steady-state electrical heating current
 U=heater voltage
 dT=temperature gradient at steady state.

It is thus seen that, as a result of the constant heater voltage and constant temperature gradient (dT), the skin blood flow is directly proportional to the heater current (I). The heater current is measured by resistor 31 and is provided as input to processing circuitry 47 via differential amplifier 30, and switch 44. Processing circuitry 47, which, for example, may be a simple amplifier, is operative to calculate the skin blood flow (V) in accordance with the above equation, and operates display 24 so as to provide a visual output indication thereof.

It is a particular feature of the present invention that the reference and the second temperatures are measured with a single temperature sensor.

In accordance with an alternative embodiment of the invention, the silicon diode, described above as preferably constituting temperature sensor 14, may also be used as a heater, by passing enough current through the silicon diode to make it self-heat. In the described self-heat mode, the silicon diode not only heats the skin, but it is also operative to measure the first and second temperatures. In this embodiment, therefore, the need for a separate heater 12, as shown and described above, is eliminated, and the functional arrangement depicted in FIGS. 2A and 2B, would thus be modified accordingly.

Figure 3:
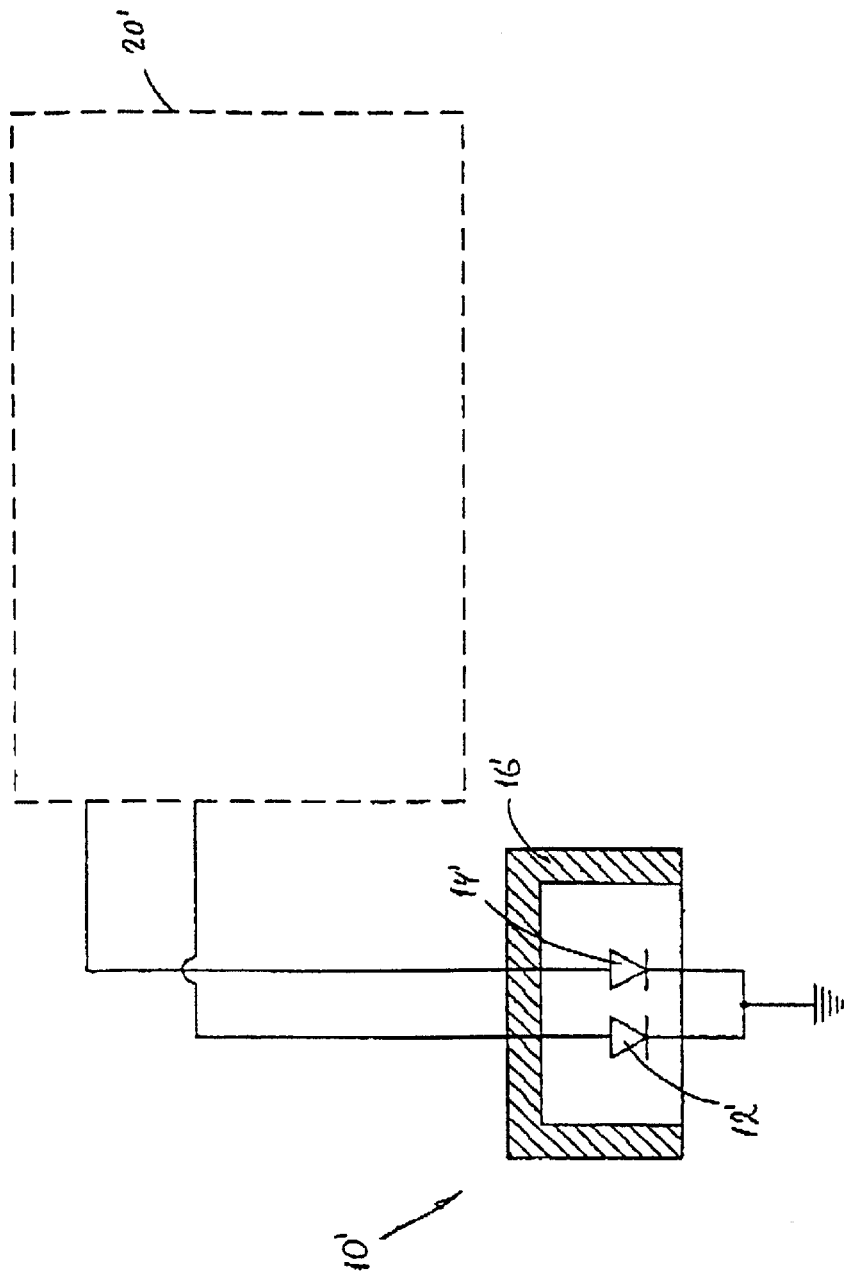
FIG. 3 is a schematic block diagram of apparatus for measuring skin blood flow, constructed and operative in accordance with the present invention, and wherein both temperature sensing apparatus and heating apparatus are constituted by silicon diodes.

Referring now briefly to FIG. 3, there is shown skin blood flow measurement apparatus, referenced generally 10', which is constructed and operative in accordance with an alternative embodiment of the present invention. The construction of apparatus 10' is similar to that of apparatus 10 (FIGS. 1, 2A and 2B), and is thus not described specifically herein, except with regards to differences between the present apparatus 10' and apparatus 10.

It is seen that both heater 12' and temperature sensor 14' are silicon diodes which are arranged as a diode array within a thermally insulating housing 16', generally similar to insulator 16, shown and described above in conjunction with FIG. 1. The apparatus also includes a control and display unit, referenced 20', which is similar to that shown and described above in conjunction with FIGS. 2A and 2B.

It will be appreciated by persons skilled in the art that the present invention, while exemplified, inter alia, by application of a positive thermal gradient to the skin, may also be implemented by application of a negative thermal gradient, namely, by cooling.

It will be also appreciated by persons skilled in the art that the present invention is not limited by what has been particularly shown and described hereinabove.

Rather the scope of the present invention is defined only by the claims which follow:

1. Apparatus for measuring skin blood flow comprising:
 means for applying a predetermined temperature gradient to a portion of skin, thereby to change the temperature thereat from a first temperature to a second temperature;
 a single temperature sensing element for measuring a temperature at a selected location near to the portion of skin;
 control means for operating said means for applying a predetermined temperature gradient and, further, for operating said temperature sensing element in first and second operative modes, in said first mode said temperature sensing element measuring a first, reference temperature at said selected location, and in said second mode said temperature sensing element being operable to measure a second temperature at said selected location, wherein, in said second mode, said control means operates said means for applying a predetermined temperature gradient so as to maintain said predetermined gradient between said first and second temperatures; and processing means, associated with said temperature sensing element, for evaluating a skin blood flow corresponding to the measured first and second temperatures and the electrical steady-state power required to maintain said predetermined temperature gradient.

2. Apparatus according to claim 1 and comprising memory means associated with said temperature sensing element for storing said reference temperature.

3. Apparatus according to claim 1, and further comprising visual display means, associated with said processing means, for displaying at least said evaluated skin blood flow.

4. Apparatus according to claim 1, and further comprising thermal insulation means for insulating said means for applying a predetermined temperature gradient and said temperature sensing element from the environment.

5. Apparatus according to claim 1, wherein said means for applying a predetermined temperature gradient comprises electrical heating means.

6. Apparatus according to claim 5, wherein said temperature sensing element comprises a silicon diode.

7. Apparatus according to claim 6, wherein said silicon diode is operative also to function as said electrical heating means.

8. Apparatus according to claim 5, wherein said electrical heating means and said temperature sensing element each comprises a silicon diode, wherein said silicon diodes are arranged in a diode array.

9. A method of measuring skin blood flow at a portion of skin, comprising the steps of:

operating a temperature sensor in touching contact with a portion of skin, so as to measure a first, reference temperature thereat;

storing the value of said first temperature;

applying a predetermined temperature gradient to the portion of skin thereby to change the temperature thereat from said first temperature to a temperature, and stabilizing the skin temperature at said second temperature;

determining the electrical power required to maintain said predetermined temperature gradient; and evaluating a blood flow associated with the portion of skin in accordance with a predetermined relationship between skin blood flow, the steady-state electrical power required to maintain said predetermined temperature gradient, and said predetermined temperature gradient.

10. A method according to claim 9, wherein said step of evaluating employs the following equation:

$$V = kIU/(dT)$$

wherein $V$ = skin blood flow $k$ = a predetermined coefficient $I$ = steady state electrical current required to maintain said predetermined temperature gradient $U$ = voltage required to maintain said predetermined temperature gradient $dT$ = said predetermined temperature gradient.

11. A method according to claim 9, wherein said step of applying a predetermined temperature gradient to the portion of skin comprises the step of electrically heating the portion of skin, thereby to increase the temperature thereat from said first temperature to an elevated, second temperature.

* * * * *